United States Patent [19]

Augustine

[11] Patent Number: 5,336,250

[45] Date of Patent: * Aug. 9, 1994

[54] THERMAL BLANKET WITH TRANSPARENT UPPER BODY DRAPE

[75] Inventor: Scott D. Augustine, Bloomington, Minn.

[73] Assignee: Augustine Medical, Inc., Eden Prairie, Minn.

[*] Notice: The portion of the term of this patent subsequent to Feb. 9, 2010 has been disclaimed.

[21] Appl. No.: 14,619

[22] Filed: Feb. 8, 1993

Related U.S. Application Data

[63] Continuation of Ser. No. 890,554, May 28, 1992, Pat. No. 5,184,612, which is a continuation-in-part of Ser. No. 703,592, May 20, 1991, Pat. No. 5,324,320, which is a continuation-in-part of Ser. No. 227,189, Aug. 2, 1988, abandoned, which is a continuation-in-part of Ser. No. 104,682, Oct. 5, 1987, abandoned.

[51] Int. Cl.⁵ .............................................. A01F 7/00
[52] U.S. Cl. ........................................ 607/107; 5/423
[58] Field of Search ............... 128/400, 367, 369, 373, 128/402, 403, 374, 380; 62/259.3; 165/46; 5/482, 485, 4, 23

[56] References Cited

U.S. PATENT DOCUMENTS 5,184,612 2/1993 Augustine ..................... 128/400

Primary Examiner—Mark S. Graham
Attorney, Agent, or Firm—Baker, Maxham, Jester & Meador

[57] ABSTRACT

A thermal blanket of the Augustine type includes an inflatable covering with a head end, a foot end, two edges and an undersurface. The covering is inflated through an inlet by a thermally-controlled inflating medium. An aperture array on the undersurface of the covering exhausts the thermally controlled inflating medium from the covering. Exhaust port openings are provided at the edges of the covering to vent the inflating medium, which enhances circulation of the thermally-controlled medium through the cover toward the periphery of the thermal blanket. A pair of uninflatable drape sections are provided at the head end for covering the chest area and enabling viewing thereof. When inflated, the thermal blanket self-erects and provides a bath of thermally-controlled inflating medium to the interior of the erected structure. When the structure covers a patient, the uninflatable transparent section at the head end provides a relatively unobstructed view of the sides of the patient's chest and upper torso.

12 Claims, 2 Drawing Sheets

THERMAL BLANKET WITH TRANSPARENT UPPER BODY DRAPE

RELATED APPLICATIONS

This is a continuation of application Ser. No. 07/890,554, filed May 28, 1992, U.S. Pat. No. 5,184,612 which is a continuation-in-part of application Ser. No. 07/703,592, filed May 20, 1991, now U.S. Pat. No. 5,324,32 which is a continuation-in-part of application Ser. No. 07/227,189, filed Aug. 2, 1988, abandoned which is a continuation-in-part of application Ser. No. 07/104,682, filed Oct. 5, 1987, abandoned: all of these related applications are incorporated herein by reference.

BACKGROUND OF THE INVENTION

This invention relates to thermal blankets used in a medical setting to deliver a bath of a thermally-controlled medium to a patient.

The thermal blanket prior art is best expressed in prior U.S. Pat. No. 4,572,188 entitled "AIRFLOW COVER FOR CONTROLLING BODY TEMPERATURE", which is assigned to the assignee of this application. In this prior patent, a self-erecting, inflatable airflow cover (the "Augustine" airflow cover) is inflated by the introduction into the Augustine cover of a thermally-controlled inflating medium, such as warmed air. When inflated, the Augustine cover self-erects about a patient, thereby creating an ambient environment about the patient, the thermal characteristics of which are determined by the temperature of the inflating medium. Holes on the underside of the Augustine airflow cover exhaust the thermally-controlled, inflating medium from inside the cover to the interior of the erected structure. This airflow cover is intended for the treatment of hypothermia, as might occur postoperatively.

Evaluation of the Augustine airflow cover by skilled practitioners has resulted in general approbation: the opinion is that the cover efficiently and effectively accomplishes its purpose of giving a thermally-controlled bath. It has been realized, however, that, while the Augustine airflow cover achieves its objective, certain improvements to it are necessary in order to realize additional clinical objectives and to enjoy further advantages in its use.

The clinical usefulness of the Augustine airflow cover has been improved by numerous developments, as set forth in the aforementioned related applications. These include controlling the contour of the inflatable portion of the cover at its head end to define a Generally concave non-inflatable portion that permits a care giver to more easily observe a patent's head, face, neck and chest. Further, venting of the thermally controlled inflating medium from the edges of the cover results in more efficient, more uniform heating within and under the cover. Modification has been made of the foot end of the cover to define a non-inflatable but erectable drape section which retains heat from the inflating medium to warm the patient's feet and insulate the bare skin of the feet from excessive heat from the inlet hose.

These improvements have resulted in an improved thermal blanket (the "Augustine" thermal blanket) in which a self-erecting inflatable covering has a head end, a foot end, two edges, and an undersurface. An inflating inlet adjacent the foot end admits a thermally-controlled inflating medium into the covering. An aperture array on the undersurface of the covering exhausts the thermally-controlled inflating medium from the covering into the structure created when the covering self-erects upon inflation. The improvements to this basic structural complement include an uninflatable section at the head end of the covering, exhaust port openings at the edges of the covering, an absorbent bib attached to the covering at the head end adjacent the uninflatable section, an uninflatable erectable drape section at the foot end of the covering, and structural features that make the covering simple and economical to produce.

With these improvements, the Augustine thermal blanket, when inflated and erected over a patient, delivers the thermally-controlled inflating medium into the interior of the structure covering the patient, thereby thermally bathing the patient. The first improvement permits full viewing of the head and face of the patient from almost any aspect around the thermal blanket. The exhaust port openings increase the rate of circulation of the inflating medium within the blanket, thereby increasing the temperature within the structure, and making the temperature distribution more uniform. The absorbent bib soaks up and retains liquids which might otherwise spread over the blanket in the area of a patient's head. Such liquids can include the patient's own perspiration, blood, vomit, saliva, or liquids which are administered to the patient. The non-inflatable erectable drape section at the foot end of the covering retains heat around the patient's feet and insulates the bare skin of the feet.

We have observed that there is a need in many instances for a thermal blanket that enables viewing the side areas of the upper torso or chest while the blanket is in place.

SUMMARY OF THE INVENTION

Therefore, the primary object of the present invention is to provide an improved Augustine inflatable thermal blanket that permits a relatively unobstructed view of a patient's chest and upper body area when in use.

Another objective is the provision of a simple and economical thermal blanket that provides efficient and uniform heating of the interior of the structure created when the blanket is inflated with a heat inflating medium.

In accordance with a primary aspect, the invention is a thermal blanket for covering and bathing a person in a thermally-controlled medium. The thermal blanket includes a flexible base sheet having a head end, a foot end, two edges, and a plurality of apertures opening through the base sheet. An overlying material sheet is attached to the first surface of the base sheet by a plurality of discontinuous seams which form the material sheet into a plurality of inflatable chambers. A continuous seam is provided between the material sheet and the base sheet at the head end to form a non-inflatable viewing area at the head end. Exhaust port openings are provided through the material sheet at the periphery of the thermal blanket to vent the medium from the chambers away from the base sheet. A continuous seam is provided between the material sheet and the base sheet at the foot end to form a non-inflatable drape section to cover the patient's feet.

These and other important objectives and advantages will become evident when the detailed description of the invention is read with reference to the below-summarized accompanying drawings, in which.

DETAILED DESCRIPTION OF THE PREFERRED EMBODIMENTS

When used herein, the term "thermal blanket" is intended to be interchangeable with, but not necessarily limited by, the term "airflow cover" used in U.S. Pat. No. 4,572,188, which is incorporated herein in its entirety by reference. In this description, the term "thermal blanket" is meant to invoke a self-erecting, inflatable structure for delivering a thermally-controlled inflating medium to the interior of the structure created when the thermal blanket is inflated. The purpose of the thermal blanket is to efficiently administer a uniformly thermally-controlled bath of the inflating medium to a patient within the erected structure.

Figure 1:
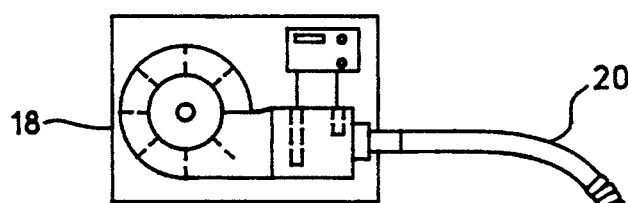
FIG. 1 is a side elevation view of a thermal blanket constructed in accordance with a preferred embodiment of the invention, with the blanket in use, with associated thermal apparatus indicated schematically.

Our invention is illustrated as we intend for it to be used in a first aspect in FIG. 1, wherein a self-erecting inflatable thermal blanket, designated generally at 10, has a head end 12, a foot end 13 and two lateral edges, indicated at 14 and 15. An inflation inlet cuff 16 is connected to an inlet port 60, and to a heater/blower assembly 18 which provides a stream of heated air or gas through a connecting hose 20. When the heater/blower 18 is operated, the stream of heated air flows through the inflating hose 20 into the thermal blanket 10 through the inflation cuff 16 and inlet port 60. When the blanket is inflated, it erects itself into a tent- or Quonset hut-like structure with a quilted upper surface 22. As described below, a pattern of apertures on the undersurface of the blanket (not shown in FIG. 1) convectively delivers the inflating heated air into the interior space enclosed by the erected thermal blanket. It also supports the thermal blanket on a cushion of heated air above the patient.

The shape of the inflatable portion of the thermal blanket 10 is narrower at the head end 12 than at the lower body of the blanket to provide an inflatable upper central portion of the blanket, with transparent side drapes 34 and 36 that cover the chest and shoulders, but allow viewing thereof.

Figure 2:
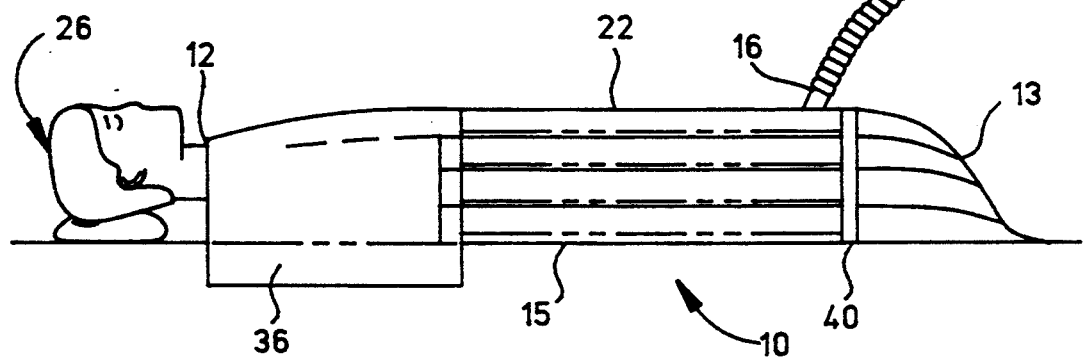
FIG. 2 is an enlarged top plan view of the thermal blanket opened flat.
Figure 2:
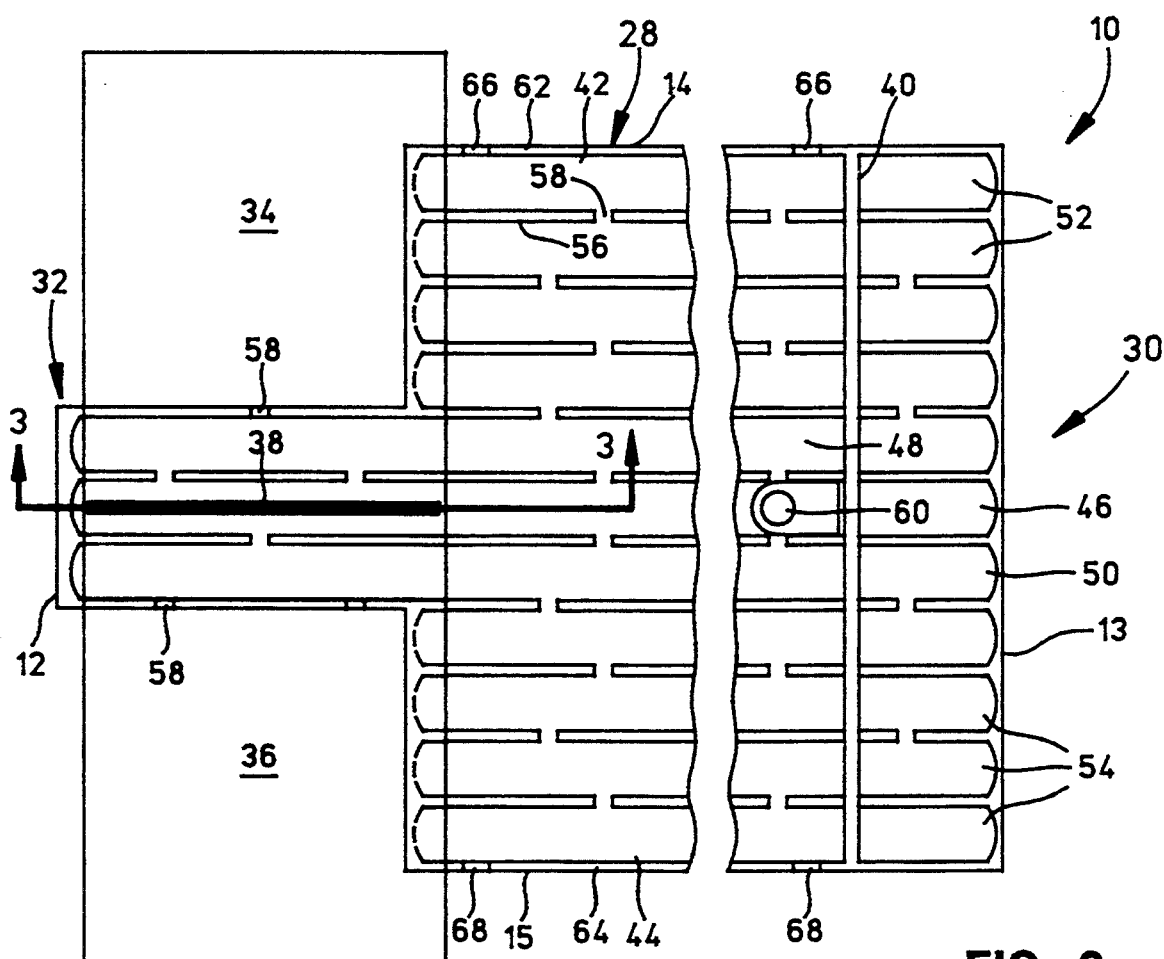

Referring to FIG. 2 of the drawings, the contour or overall shade of the inflatable portion of the thermal blanket 10 will be apparent. This overall shape includes a large generally rectangular lower body portion, designated generally at 28, and a narrower elongated rectangular upper body portion. The upper body portion includes an inflatable portion, designated generally at 60 32, having a width substantially less than the width of the portion 28, but sufficient to cover only the top or front portion of the chest of a patient 26. The side portion of the chest is covered by a pair of transparent lateral panels or drapes 34 and 36. The drape portions 34 and 36 are secured along a center line 38 to the top of the upper body inflatable portion 32, and overlap the top edge of the lower body inflatable portion as shown.

These are secured only along the strip 28, as illustrated, and may be pulled up to gain access to the sides of the body and chest area of the patient.

The inflated section of the blanket is formed of tubes, as described in the related applications and in the illustrated embodiment. The foot drape portion 30 may be formed simply by sealing across a lower or foot section of the main body portion along a line 40. Thus, the overall blanket is pre-formed with the tubes, but the lower ends of the tubes for the foot drape section are rendered uninflatable being sealed off just below port 60 from the upper portion of the tubes.

As illustrated in FIG. 1, the thermal blanket of the invention when inflated erects itself into a bathing structure, and bathes the patient 26 with the thermally controlled air used to inflate the structure. While the patient is being bathed, the uninflated lateral drape panels 34 and 36 overlie the side of the body, chest and arms of the patient and permit observation of the patient's upper body and chest area. The transparent drape panels 34 and 36 serve to confine and trap the thermally controlled air in and around the patient's upper torso, permitting it to escape around the edges thereof.

With reference to FIG. 2, a top view of the thermal blanket 10 is illustrated in an open flat position to show details of its structure and configuration. The upper surface of the thermal blanket illustrates a parallel array of elongated tubes, of which tubes 42 and 44 are the lateral most tubes of the inflatable lower body portion. Tube 46 is a central tube that runs through the lower body as well as central of the upper body portion 32. Closely adjacent lateral tubes 48 and 50 extend through the lower body and through the upper body, forming the lateral most tubes of the upper body portion. Intermediate tubes 52 extend between tubes 42 and 48 on one side of the lower portion of the lower body portion, and tubes 54 are disposed between elongated tube 50 and 44 on the other side of the lower body portion.

Each tube in the array is separated from an adjacent tube by discontinuous seams, one of which is indicated at 56. The seam 56 separates the tube 42 from its nearest adjacent neighbor, with the seam being interrupted by passageways (one indicated by reference numeral 58) communicating between the tubes. The discontinuities of the elongate seams, such as the seam 56, form the passageways 58 that extend between adjacent tubes. The seams permit the thermal blankets when inflated to assume the tubular structure on the upper surface, while the ports or passages 58 permit full circulation of the inflating medium between tubes. The foot end seam 40 is continuous; it seals the ends of the inflatable tubes and separates the foot drape portion of the lower body portion of the thermal blanket into a non-inflatable foot drape section. The inflatable section of the tubes are inflated through the center tube 46, which transitions to a port 60 through which the inflation cuff 16 is inserted.

The edge seams 62 and 64 at the periphery of the thermal blanket are discontinuous to form exhaust ports or vents 66 and 68 on opposite side edges. A seal can be made between the inflation port 60 and the cuff 16 by any suitable means, such as an 0-ring or a tape. When the inflating medium is introduced into the center tube 46, it flows laterally from the center tube into all the other tubes through the ports or openings 58 between the adjacent tubes. The circulation of the medium to the edges of the blanket is continuously supported by the vents 66 and 68 while the thermal blanket is inflated.

The rectangular shaped top or upper body portion 32 of the thermal blanket 10 forms a primary chest cover, with the non-inflatable drapes 34 and 36 forming lateral drapes or covers that cover sides of the upper torso. Thus, the entire chest area is bathed with thermally controlled medium, with the drapes 34 and 36 aiding in confining the thermally controlled medium to the upper body area before it escapes around the side edges of the drapes. It should also be understood that the pattern of inflatable tubes can be replaced by other suitable patterns of communicating inflatable chambers. However, the longitudinally extending tubes, as illustrated, are preferred since they impart strength and shape to the erected bathing structure.

Figure 3:
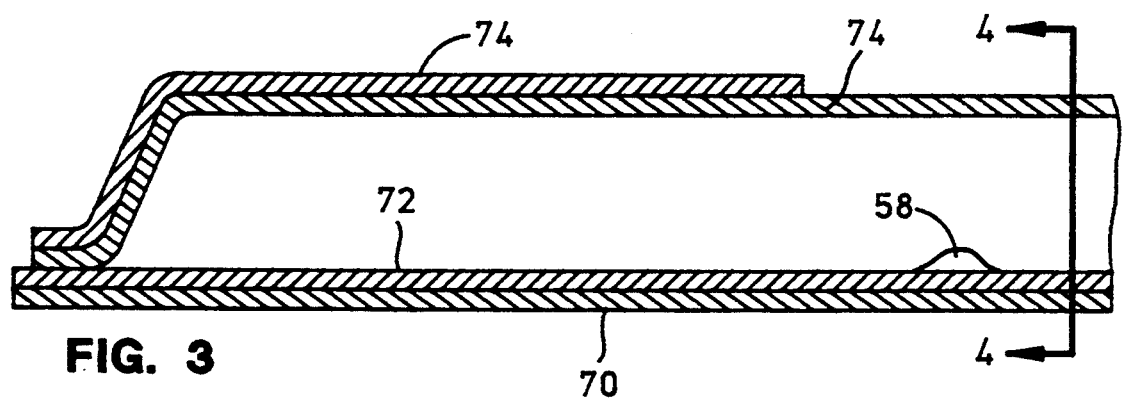
FIG. 3 is an enlarged sectional view taken along 3—3 of FIG. 2.
Figure 4:
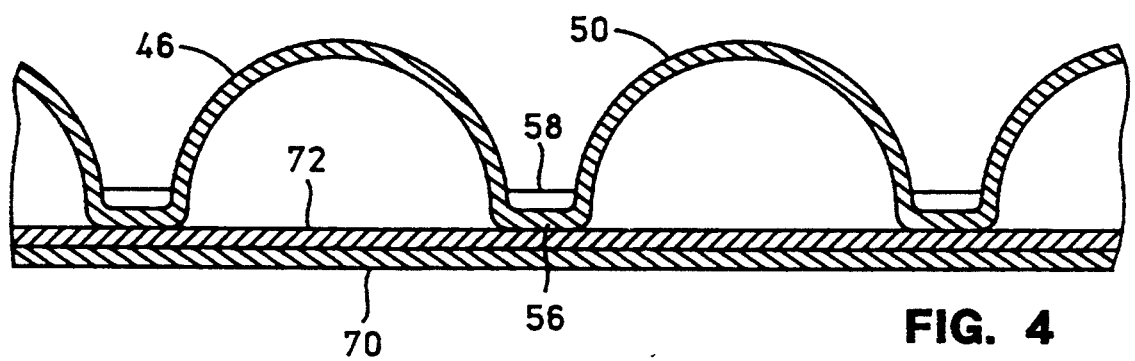
FIG. 4 is a further enlarged sectional view taken along line 4—4 of FIG. 3.

Referring to FIGS. 3 and 4 of the drawings, details of construction of the thermal blanket are illustrated. The thermal blanket 10 is assembled from a base sheet consisting of an underside layer or sheet 70, formed from flexible material capable of bonding to a layer 72 or thin film of heat sealable plastic. For the layers 70 and 72, a stratum of absorbent tissue paper pre-laminated with a layer of heat sealable plastic film has been used. Material of such construction is commercially available in production rolls and is used to make painter's drop cloths. This forms a thin lightweight base sheet.

Figure 5:
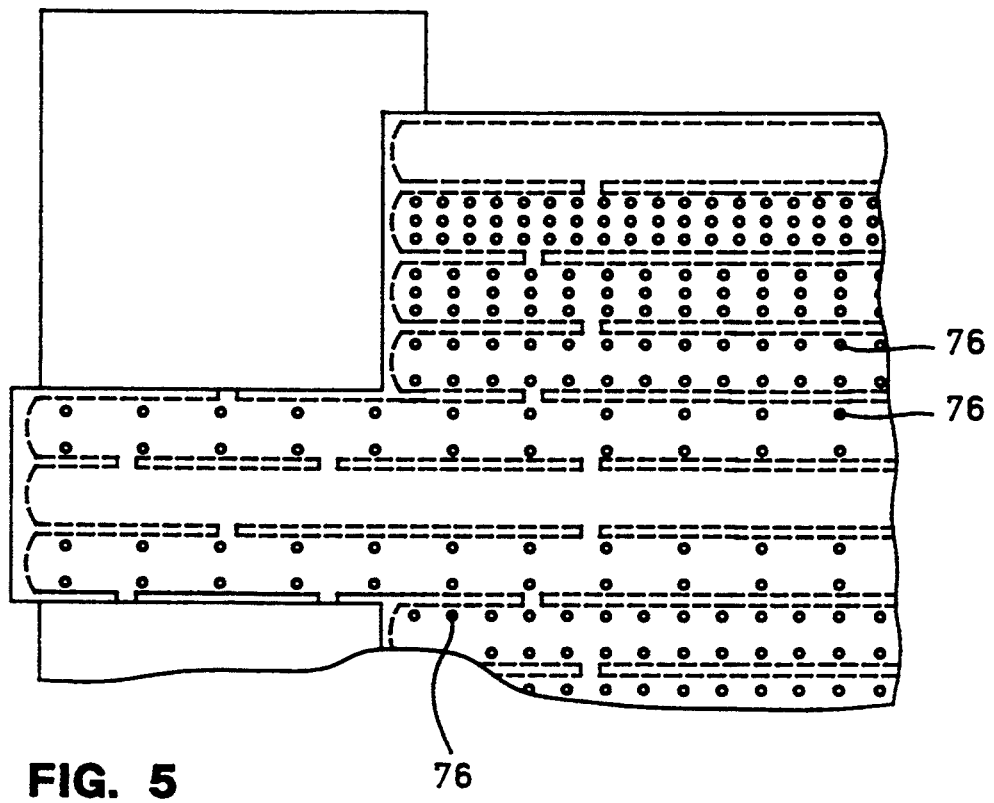
FIG. 5 is a partial underside view of the thermal blanket.

The upper or top side of the thermal blanket consists of a thin sheet of thin plastic film that has an initial width greater than the base sheet and that is bonded to the plastic layer 72 by a heat sealing process to form the interrupted seams 56, one of which is indicated at 56 between inflatable tubes 46 and 50. The excess width of the top material sheet 74 enables the formation of the tubes 46, 50, etc., as shown in FIG. 4. The top sheet 74 is preferably formed of a very thin film of polymer plastic. As can be seen in FIG. 3, the interruption of this seam 56 forms a passageway 58 between adjacent tubes 46 and 50. As can be seen in FIGS. 2 and 5, the interruptions are staggered in order to force a more uniform distribution of the thermally controlled medium in the tubes and throughout the thermal blanket.

The central upper body portion of the inflatable portion of the thermal blanket may be provided with an uninflatable bib extension portion, as disclosed and discussed in related applications.

Circulation of the heated medium throughout the blanket is enhanced by the vents 66, which may be provided at the outermost corners of the inflatable portion of the thermal blanket. The vents 66 and 68 vent the heated inflating air out of the outermost tubes 42 and 44 away from the underside of the blanket. Because the air can circulate to and through the blanket edges, the inflating air in the outermost tube is hotter than if the openings were absent. This results in hotter air being delivered throughout the underside apertures toward the edge of the blanket.

The temperature distribution within the thermal blanket has been measured for inflating air which is heated to a medium temperature range and for inflating air which is heated to a high temperature range. The results are provided in Table 1 for a blanket consisting of thirteen tubes.

TABLE I

| TUBE NO. | MEDIUM TEMPERATURE RANGE | | HIGH TEMPERATURE RANGE | |
|---|---|---|---|---|
| | WITHOUT EXHAUST PORTS | WITH 2" EXHAUST PORTS | WITHOUT EXHAUST PORTS | WITH 2" EXHAUST PORTS |
| center (inlet) tube | 113.3° F. | 114.1° F. | 121.3° F. | 121.3° F. |
| Tube #1 | 109.9° | 112.3° | 117.3° | 117.7° |
| Tube #2 | 105.3° | 109.8° | 113.4° | 115.0° |
| Tube #3 | 103.2° | 107.1° | 111.0° | 113.3° |
| Tube #4 | 99.9° | 104.3° | 101.4° | 108.6° |
| Tube #5 | 97.2° | 100.0° | 95.7° | 104.4° |
| Tube #6 (outermost) | 85.2° | 95.8° | 89.6° | 99.4° |
| Average temp. under cover | 103.8° | 106.7° | 108.4° | 112.5° |

Measurements of the temperature of air exhausted through underside apertures were made on the underside of each tube on one side of the blanket. The tubes are numbered 1–6, with 1 being the tube adjacent the center tube, and tube 6 being the outermost tube adjacent and on the lateral edge of the blankets. Test apertures were made in the bottom of tube 6 only for the purpose of this test. As is evident, the distribution of temperature within the erected thermal blanket is more uniform when the exhaust port openings are provided. Further provision of the exhaust ports also increases the average temperature within the erected structure of the blanket. Thus, the provision of exhaust port openings at the lateral edges of the blanket delivers results which one would not expect when considering the operation of our thermal blanket with no exhaust port openings.

Preferably, the exhaust port openings are slits in the edge seam of the blanket. These slits vary in length from one and three-quarters to two inches. Each edge seam is discontinuous proximate each corner of the blanket, so that air is vented away from the underside of the erected blanket. This keeps relatively colder air at the blanket edges from mixing with the relatively hotter air exhausted into the structure through the underside apertures. The result is a flatter temperature profile of air within the blanket than would exist without the vents. This raises the average temperature within the erected structure and makes the temperature distribution in the structure more uniform throughout. Thus, heating is better controlled and more uniform with greater comfort to the patient, thus enhancing the clinical effect of the thermal blanket.

Referring now to FIGS. 4 and 5, the thermal blanket of the present invention is enabled to bathe a patient in the thermally controlled inflating medium introduced into the upper side tubes by means of a plurality of apertures 76. The apertures extend through the layers 70 and 72 of the underside of the blanket. The apertures 76 are formed in the footprints of the tubes of the blanket according to a pattern which has been determined to deliver a very uniform thermal bath. In this regard, the apertures 76 may be provided through the underside to the aperture tubes in a density which varies inversely with the proximity of the tube to the center tube, as illustrated in FIG. 5. Thus, the hole density increases from the center tube 46 to the edges of the blanket.

Even with the exhaust port openings 66 and 68, the temperature of the inflating medium exhibits a drop from the center to the lateral most tubes.

The varying density of the apertures 76 tends to reduce this gradient further by forcing hotter air to the edges of the blanket. Thus, the thermal bath delivered to the patient is of a generally uniform temperature throughout the area of coverage. The aperture density variation also equalizes the flow of inflating medium out of the apertures. As will be evident, the inflating pressure will be greater at the center tube 46 and will tend to diminish toward the lateral edges of the thermal blanket. Therefore, the fewer apertures are required for the tube near the center tube 34 to deliver the same amount of air as the relatively greater number of apertures in the tubes at a greater distance from the center tube 46.

The apertures comprise openings which can be of any suitable shape. For example, we have produced blankets with elongated apertures approximately one-quarter inch in length. These may be larger or smaller and may also vary accordingly in density to achieve the desired distribution.

The invention is illustrated with a foot drape. However, the blanket may be formed without the foot drape, or the foot drape may be modified to have other structure and configurations. In the illustrated embodiment, the foot drape is formed simply by sealing off the lowermost ends of the inflatable tubes by a sealing seam 40 that extends across the bottom edge of the thermal blanket. Thus, the lowermost ends of the tubes are not inflated, resulting in a generally pliable, flexible drape portion when the blanket is inflated.

The laterally extending shoulder drapes of the thermal blanket are non-inflatable but are erectable, that is supportable under the force of the heated medium circulating around the upper torso of the patient. The drapes thus trap and retain the heated medium around the patient's shoulders and chest area. The drape is preferably transparent to enable viewing of the sides of the chest and upper torso area of the patient without disturbing the cover.

While I have illustrated my invention by means of specific embodiments, it will be evident to those skilled in the art that many variations and modifications may be made therein. However, it is to be understood that the scope of the present invention is to be limited only by the appended claims.

I claim:

1. A thermal blanket for covering and bathing a person in a thermally-controlled inflating medium, comprising:
    a flexible base sheet having top and bottom surfaces, a head end, a foot end, two side edges, and a plurality of apertures therethrough;
    an overlaying top sheet attached to a first surface of said base sheet by a plurality of seals which form said overlaying top sheet into a plurality of communicating, inflatable chambers, said apertures opening through said base sheet into said chambers;
    said base sheet and said top sheet forming an inflatable generally rectangular lower main body section of a first width and an inflatable generally rectangular upper central body section forming a chest cover extension at said head end having a second width less than said first width; and
    a non-inflatable transparent chest drape formed by lateral extensions of a film sheet extending laterally from said central body section.

2. The thermal blanket of claim 1 wherein said non-inflatable transparent chest drape is formed by a generally rectangular transparent sheet of polymer film secured to said upper central body section.

3. The thermal blanket of claim 1 wherein said base sheet includes a laminated structure in which a bottommost paper layer is bonded to an upper layer of plastic material, and said seals are formed between said overlaying top sheet and said upper layer of said plastic material.

4. A thermal blanket for covering and bathing a person in a thermally-controlled flow of air and providing visibility to the person's upper body, comprising:
    a inflatable covering with a head end, a foot end, two edges, and an undersurface, the inflatable covering having a configuration including a generally rectangular lower main body section and an inflatable generally rectangular upper central body section forming a continuous extension of a central portion of said lower main body section and defining a chest cover of a width less than the width of said lower main body section;
    an inflating inlet in said inflatable covering for admitting a thermally-controlled inflating medium into said inflatable covering;
    an array of apertures in said undersurface adapted for exhausting said thermally controlled inflating medium from said inflatable covering; and
    a non-inflatable transparent upper body drape secured to and extending laterally beyond said central body section.

5. The thermal blanket of claim 4 wherein said non-inflatable transparent upper body drape is formed by a generally rectangular transparent sheet of polymer film secured to said upper central body section.

6. The thermal blanket of claim 4 further including a non-inflatable foot drape at said foot end.

7. A system for delivering a bath of thermally controlled medium to a patient for controlling the temperature of the patient comprising:
    means for delivering a supply of thermally-controlled air;
    a thermal blanket for covering a bathing a person in a thermally-controlled inflating medium, said thermal blanket detachably connected to said means for delivering, wherein the thermal blanket comprises:
        a flexible base sheet having top and bottom surfaces, a head end, a foot end, two side edges, and a plurality of apertures therethrough;
        an overlaying top sheet attached to a first surface of said base sheet by a plurality of seals which form said overlaying top sheet into a plurality of inflatable chambers, said apertures opening through said base sheet into said chambers; and
        said base sheet and said top sheet forming an inflatable generally rectangular lower main body section of a first width and an inflatable generally rectangular upper centrally body section forming a chest cover extension at said head end having a second width less than said first width; and
    a non-inflatable upper-body drape formed by extensions of an overlying transparent film sheet extending outwardly from said central body section.

8. A thermal blanket for covering and bathing a person in a thermally-controlled inflating medium, comprising:

a flexible base sheet having top and bottom surfaces, a head end, a foot end, two side edges, and a plurality of apertures therethrough;

an overlaying top sheet attached to a first surface of the base sheet at a plurality of locations to form a plurality of passageways for circulating an inflating medium between the top sheet and the base sheet;

the base sheet and the top sheet forming an inflatable generally rectangular lower main body section of a first width and an inflatable generally rectangular upper central body section forming a chest cover extension at the head end having a second width less than the first width; and a non-inflatable chest drape extending laterally from the central body section.

9. The thermal blanket of claim 8, wherein the non-inflatable chest drape is formed by a generally rectangular transparent sheet of polymer film secured to the upper central body section.

10. The thermal blanket of claim 8, wherein the base sheet includes a laminated structure in which a bottommost paper layer is bonded to an upper layer of plastic material, and the seals are formed between the overlaying top sheet and the upper layer of the plastic material.

11. The thermal blanket of claim 10, wherein non-inflatable upper body drape is formed by a generally rectangular transparent sheet of polymer film attached to the upper central body section.

12. The thermal blanket of claim 11, further including a non-inflatable foot drape at the foot end.

* * * * *

UNITED STATES PATENT AND TRADEMARK OFFICE
CERTIFICATE OF CORRECTION

PATENT NO.   : 5,336,250
DATED        : August 9, 1994
INVENTOR(S)  : Augustine

It is certified that error appears in the above-indentified patent and that said Letters Patent is hereby corrected as shown below:

Column 8, line 63, please change "centrally" to --central--.

Signed and Sealed this

Twenty-seventh Day of December, 1994

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,336,250
DATED : August 9, 1994
INVENTOR(S) : Scott D. Augustine

It is certified that error appears in the above-identified patent and that said Letters Patent is hereby corrected as shown below:

Title page,
Item [63], after "Pat. No. 5,324,320, which is a continuation", please delete "-in-part".

Column 1,
Line 10, after "5,324,320 which is a continuation", please delete "-in-part".

Signed and Sealed this

Fourth Day of February, 2003

JAMES E. ROGAN
*Director of the United States Patent and Trademark Office*